US00PP10116P

United States Patent [19]

Gerawan

[11] Patent Number: Plant 10,116

[45] Date of Patent: Nov. 11, 1997

[54] "7-B" PLUM TREE

[76] Inventor: Michael R. Gerawan, 6407 Englehart, Reedley, Calif. 93654

[21] Appl. No.: 593,529

[22] Filed: Jan. 24, 1996

[51] Int. Cl.[6] ..... A01H 5/00

[52] U.S. Cl. ..... Plt./38.1

[58] Field of Search ..... Plt./38.1

[56] References Cited

U.S. PATENT DOCUMENTS

P.P. 2,539 6/1965 Anderson ..... Plt./38.1

*Primary Examiner*—James R. Feyrer

*Attorney, Agent, or Firm*—Worrel & Worrel

[57] ABSTRACT

A new and distinct variety of plum tree *Prunus salicina*, which is somewhat similar to the "Red Beaut" plum tree (U.S. Plant Pat. No. 2,539) in the production of fruit of similar size, shape, color and date of maturity, as well as in other respects, but from which it is distinguished in a number of respects including by producing abundant pollen which substantially enhances is ability to set a crop.

1 Drawing Sheet

BACKGROUND OF THE NEW VARIETY

The present invention relates to a new and distinct variety of plum tree, which will hereinafter be denominated varietally as the "7-B" plum tree, and, more particularly, to a plum tree which produces fruit, which are mature for commercial harvesting and shipment approximately May 25 to June 8 in the San Joaquin Valley of central California.

A problem inherent to one degree or another with virtually all commercial varieties of fruit trees is pollination. Obviously, without adequate pollination, crop production is inadequate. With some commercial varieties of tree fruit, this is a chronic problem.

The "Red Beaut" plum tree (U.S. Plant Pat. No. 2,539) is pollen sterile. Experience has taught, since is introduction in 1965, that the "Red Beaut" cultivar frequently sets light crops. While the fruit produced by the "Red Beaut" plum variety is commercially successful, it has earned a reputation among growers for being a plum variety on which it is difficult to set a crop.

As a consequence, considerable effort has been devoted to improving upon the pollination characteristics of the "Red Beaut" plum tree in commercial farming operations. For example, growers have grafted the wood of other plum varieties directly onto each "Red Beaut" plum tree in their orchards to produce limbs for pollination of the "Red Beaut" variety. These "*pollinator limbs*" have only been partially successful in achieving the desired result due to the fact that the pollen sterile flowers of the "Red Beaut" plum variety remain unatractive to the bees, even though they have collected pollen from the flowers of the pollinator limbs. Due to the expense involved in establishing pollinator limbs and the marginal success thereof, the "Red Beaut" plum variety is not as commercially successful as would otherwise be the case.

Therefore, it has long been recognized that it would be desirable to have a variety of plum tree having all the attractive characteristics of the "Red Beaut" cultivar, but which possesses improved pollination capabilities. The new plum variety of the present invention appears to be such a cultivar.

ORIIGIN AND ASEXUAL REPRODUCTION OF THE NEW VARIETY

The variety was discovered as a sport of the variety 'Red Beaut' by the inventor in April, 1986 near Reedley, in the San Joaquin Valley of central California. The new variety was first asexually reproduced by grafting wood of the new variety onto Nemaguard rootstock in February, 1987. This was performed in Reedley, Calif. at the inventor's direction. The inventor has continued to observe the progeny of the new variety since 1987 and has confirmed that they are in all respects identical to the parent tree.

SUMMARY OF THE NEW VARIETY

The "7-B" plum tree is characterized by producing semi-clingstone fruit which are very early maturing and of medium size having a uniform garnet purple skin coloration and ripening for commercial harvesting and shipment approximaely May 25 to June 8 in the San Joaquin Valley of central California. The new variety is most closely similar to the "Red Beaut" plum tree (U.S. Plant Pat. No. 2,539), but is distinguished therefrom in a number of respects including its abundant production of pollen substantitally enhancing its capability for setting a crop as compared with the "Red Beaut" plum variety.

BRIEF DESCRIPTION OF THE DRAWING

In the top photograph:

A stem of fruiting wood in a stage of full bloom is depicted, and shows numerous blooms at a stage approaching anthesis, with petals, sepals and reproductive organs being illustrated in large scale.

In the bottom photograph:

The drawing is a color photograph showing mature fruit of the new variety of plum tree of the present invention including a first in bottom plan view showing the apex thereof; a second in side elevation; a third in side elevation showing the suture thereof; a fourth in top plan view showing the base thereof; a fifth sectioned and laid open to expose the flesh thereof and with the stone cavity exposed in one section and the stone in place in the other section thereof; and representative foliage, all of the new variety.

DETAILED DESCRIPTION

Referring more specifically to the pomological details of this new and distinct variety of plum tree, the following has been observed under the ecological conditions prevailing at the orchard of origin which is located near Sanger, Calif. All major color code designations are by reference to the

*Dictionary of Color*, by Maerz and Paul, First Edition, 1930. Common color names are also occasionally employed.

TREE

Generally:

*Size.*—Large.

*Vigor.*—Vigorous and in the upper range for a Japanese plum species.

*Chilling requirements.*—Hardy under typical number of days of chilling experienced in the San Joaquin Valley of central California.

*Figure.*—Upright spreading to broadly spreading and can be substantially modified by pruning.

*Productivity.*—This tree will be more likely to be, or is, more productive than the parent tree 'Red Beaut' by its characeristic copious pollen production and apparent self-pollination capacity.

*Regularity of bearing.*—Regular.

Trunk:

*Size.*—Large in diameter.

*Surface texture.*—Moderately rough, developing a moderate amount of scarfskin.

*Color.*—Grey (7-C-8) to grey-brown (7-H-9).

*Lenticels — numbers.*—Numerous.

*Lenticels — size.*—Medium.

Branches:

*Size.*—Slightly above average in caliper.

*Surface texture.*—Medium.

*Color — mature branches.*—Dark grey-brown (8-H-9).

*Color — immature branches.*—Medium green (21-K-7) and are tinged with red coloration on shoots exposed to direct sunlight and on vigorous shoots at the shoot terminal.

LEAVES

Size:

*Generallly.*—Large. Leaf measurements have been taken from leaves growing at midpoint of vigorous upright growing shoots of current season's growth. These leaves are in the largest size range on the tree.

*Average length.*—Averages 12.8 cm (5.12 inches) including the petiole.

*Average width.*—Averages 5.3 cm (2.12 inches).

Form: Usually moderately obovate, although some variability exists. The apex of the leaf is acute and often slightly twisted.

Color:

*Upwardly disposed surface.*—Dark green (23-L-8).

*Downwardly disposed surface.*—Lighter grey-green (22-K-7). The immature terminal leaves are characteristically tinged an orange-green, becoming fully green with maturity.

Leaf margin: Strongly crenate with coarse crenations and often doubly crenate at mid-margin.

Petiole:

*Size.*—Medium.

*Length.*—Averages 11 mm (0.44 inches) to 14 mm (0.56 inches).

*Thickness.*—Averages 2.0 mm (0.08 inches).

*Color.*—Light green (20-J-4), often slightly tinged with red, especially basally.

Leaf glands:

*Size.*—Small to medium.

*Form.*—Somewhat variable. The stalked glands are most often globose in form.

*Position.*—Usually two reniform glands occur in alternate position at the base of the leaf margin.

*Pattern.*—An occasional stalked gland in present adjacent to the base of the leaf blade and positioned on the petiole. The leaf glands are most often reniform although nearly globose types can be present.

*Color.*—Shiny green (19-L-7), darkening and deteriorating with age.

Stipules: Small.

*Length.*—Averaging 5 mm (0.2 inches) to 6 mm (0.24 inches).

*Form.*—Lanceolate.

*Color.*—Light green (18-K-6).

*Margin.*—Coarsely serrate in form. The stipules are early deciduous.

FLOWERS

Flower buds: Hardy under typical San Joaquin Valley climatic conditions. This description was produced from flowers obtained from trees of the subject variety growing in a test orchard near Sanger, Calif. There were 1195 hours of chilling recorded near Sanger in Fresno County, Calif. during the 1991–1992 season. This number of hours at or below forty-five degrees (45°) Fahrenheit represents a normal to slightly higher than normal winter chilling season.

*Size.*—Medium.

*Surface Texture.*—Nearly glabrous.

*Form.*—Conic and the buds are slightly appressed to the stem.

Flower bud scales: Color — Dark brown (Falcon brown 8J-10).

Date of bloom: Early in relation to other common commercial plum varieties, but occurs at the same time as the standard "Red Beaut" plum tree. The date of first bloom was Feb. 23 in 1992. Date of full bloom was Feb. 28 in 1992.

Size:

*Generally.*—Medium. From 18 mm (0.72 inches) to 20 mm (0.8 inches) when fully expanded. Flowers often remain slightly cupped inwads even when fully expanded.

Bloom quantity: Abundant. Most commonly there are four flowers per node.

Petals:

*Color.*—White (1-A-1).

*Size.*—Medium and five per flower.

*Length.*—Averages from 9 mm (0.36 inches) to 11 mm (0.44 inches).

*Width.*—Averages from 8 mm (0.32 inches) to 10 mm (0.4 inches).

*Form.*—Variable from oval to slightly ovate.

Petal claw — Form: Short and truncate.

Petal — Margin: Substantially undulate, more strongly so at the petal apices.

Petal Apices:

*Form.*—Variable, from smoothly rounded to slightly raised.

Pedicel:

*Length.*—Averages from 11 (0.44 inches) to 13 mm (0.52 inches).

*Thickness.*—Averages 1.0 mm (0.04 inches).

*Color.*—Light green (18-J-4).

*Surface.*—Glabrous.

Nectaries:
*Color.*—Greenish brown (13-K-6) when young, becoming more dull in color with age.
Calyx:
*Surface.*—Usually glabrous.
*Color.*—Light green (18-J-5).
Sepals:
*Size.*—Medium.
*Color.*—Exterior a light green (18-G-6). Interior a slightly darker green (18-I-6).
Anthers — size: Medium.
Anthers — color: Orange-yellow (Saratoga yellow 11-J-8) ventrally and dorsally.
Anthers — margins — color: Reddish (Ember red 5-K-10), especially ventrally.
Pollen: Abundant.
*Color.*—Bright yellow (10-K-5).
Stamens:
*Length.*—Variable, from 6 mm (0.24 inches) to 8 mm (0.32 inches). Stamens usually slightly shorter than pistil when fully extended.
*Color.*—White (1-A-1).
Pistil: Length.—Averages 10 mm (0.4 inches), including ovary.
*Color.*—Very light green (18-H-2).
*Surface.*—Glabrous.

FRUIT

Maturity when described: Ripe for commercial harvesting and shipment approximately May 25 to June 8 near Sanger in the San Joaquin Valley of central California.
Size:
*Generally.*—Medium.
*Average diameter in the axial plane.*—50 mm (2.0 inches).
*Average diameter transverse in the suture plane.*—50 mm (2.0 inches).
*Average diameter in the check plane.*—51 mm (2.04 inches).
*Form.*—Broadly ovate in lateral aspect. Fruit is globose in apical aspect.
*Form — uniformity.*—Good.
*Form — symmetry.*—Variable from symmetrical to slightly asymmetrical.
*Suture — generally.*—Expresses itself as a shallow, thin line present from the apex to the base. The suture has no specific color of its own, but blends with and matches the surrounding skin coloration.
*Ventral surface — generally.*—Rounded and quite smooth with very little lipping.
*Stem cavity — generally.*—Small and moderately deep.
*Stem cavity — width.*—Averages from 16 mm (0.64 inches) to 21 mm (0.84 inches).
*Stem cavity — depth.*—Averages from 9.5 mm (0.38 inches) to 10.5 mm (0.42 inches).
*Stem cavity — length.*—Averages from 20 mm (0.8 inches) to 23 mm (0.92 inches).
*Stem cavity.*—Shape — Oval.
*Stem — color.*—Light green to brownish (21-J-3 to 15-J-8).
*Stem — length.*—Medium from 11 mm (0.44 inches) to 14 mm (0.56 inches).
*Stem — thickness.*—Averages 2.0 mm (0.08 inches).
*Base.*—Variable from slightly truncate to at times rounded. Angle of base at right angle to the fruit axis.
*Apex — shape.*—Rounded to very slighty raised.
*Pistil point.*—Usually slightly oblique.
Skin:
*Thickness.*—Average.
*Texture.*—Glabrous and tenacious to the flesh.
*Tendency to crack.*—None.
*Flavor.*—Skin is mild with very little acidity.
*Color.*—Uniform garnet purple (7-J-6). Fruit surface is smooth and regular with only a few small light colored dots present over the apex.
*Ground color.*—No ground color is present at full maturity. A light grey bloom is present, uniformly spread over the entire fruit surface.
Flesh:
*Flesh color.*—Interior color is a light amber yellow (10-K-5).
*Surface of pit cavity.*—Slightly darker amber brown (12-F-8). A moderate number of light colored fibers are present in the flesh. These fibers are fine textured and moderately long.
*Flavor.*—Mild and low acid. The fruit is sweet and of a pleasant flavor.
*Aroma.*—Only a slight aroma is present at commercial maturity.
*Ripening.*—Ripens evenly.
*Eating quality.*—Good.
Stone:
*Attachment.*—Semi-clingstone. Flesh fibers adhere to stone, expecially laterally over the stone surface.
*Fibers — numbers.*—Numerous fibers are present, usually attached laterally to the stone.
*Fibers — length.*—Short.
*Size — generally.*—Small.
*Size — length.*—17.5 mm (0.9 inches) to 18 mm (0.72 inches).
*Size — width.*—16.0 mm (0.64 inches) to 16.5 mm (0.66 inches).
*Size — Thickness.*—8.5 mm (0.34 inches) to 9.0 mm (0.36 inches).
*Form — generally.*—Somewhat irregular, from ovate to nearly oval.
*Apex — shape.*—Generally rounded with a low sharp tip.
*Color — Dry.*—Light tan (10-H-6).
*Base — shape.*—Broad, rounded on the ventral suture side and rounded to truncate on the dorsal suture side. Base angle is most frequently very slightly oblique to the stone axis, but some variability in base angle does exist.
*Sides — generally.*—Variable, but most often slightly unequal.
*Hilum.*—Small and narrow with substantial erosion present.
*Surface.*—Moderately smooth with a pattern of low netted ridges over the lateral surfaces. A series of grooves present over the basal shoulder area, converging basally.
*Ventral edge.*—A prominent narrow wing present from apex to base, more prominent in the area from mid-suture to the base. A moderately wide and deep groove, at times discontinuous, is present roughly parallel to the ventral edge, 3 mm (0.12 inches) to 4 mm (0.16 inches) below the edge and converging apically and basally. Other smaller grooves can be present in the same general area, but are usually less prominent. The basal 4 mm (0.16 inches) to 5 mm (0.2 inches) of the ventral edge is substantially eroded.

*Dorsal edge.*—A characteristically wide groove is present along the dorsal edge from the base of the stone to well above mid stone. The two ridges subtended by the groove are rather jagged or scalloped. The dorsal suture narrows to just a thin edge from above mid stone to the apex.

*Tendency to split.*—No tendency to split observed.

Use: Fresh market.

Shipping and handling qualities: Suitable for both local markets and for long distance shipping.

Although the new variety of plum tree possesses the described characeristics noted above as a result of the growing conditions prevailing near in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of plum tree, what I claim as new and desire to be secured by Plant Letters Patent is:

1. A new and distinct variety of plum tree substantially as illustrated and described which produces very early maturing, medium sized fruit with bright purple-red skin coloration, mild flavor and very vigorous tree growth and which is sonewhat similar to the "Red Beaut" plum tree (U.S. Plant Pat. No. 2,539), from which it was derived, but from which it is distinguished in a number of respects including that it produces abundant pollen.

* * * * *

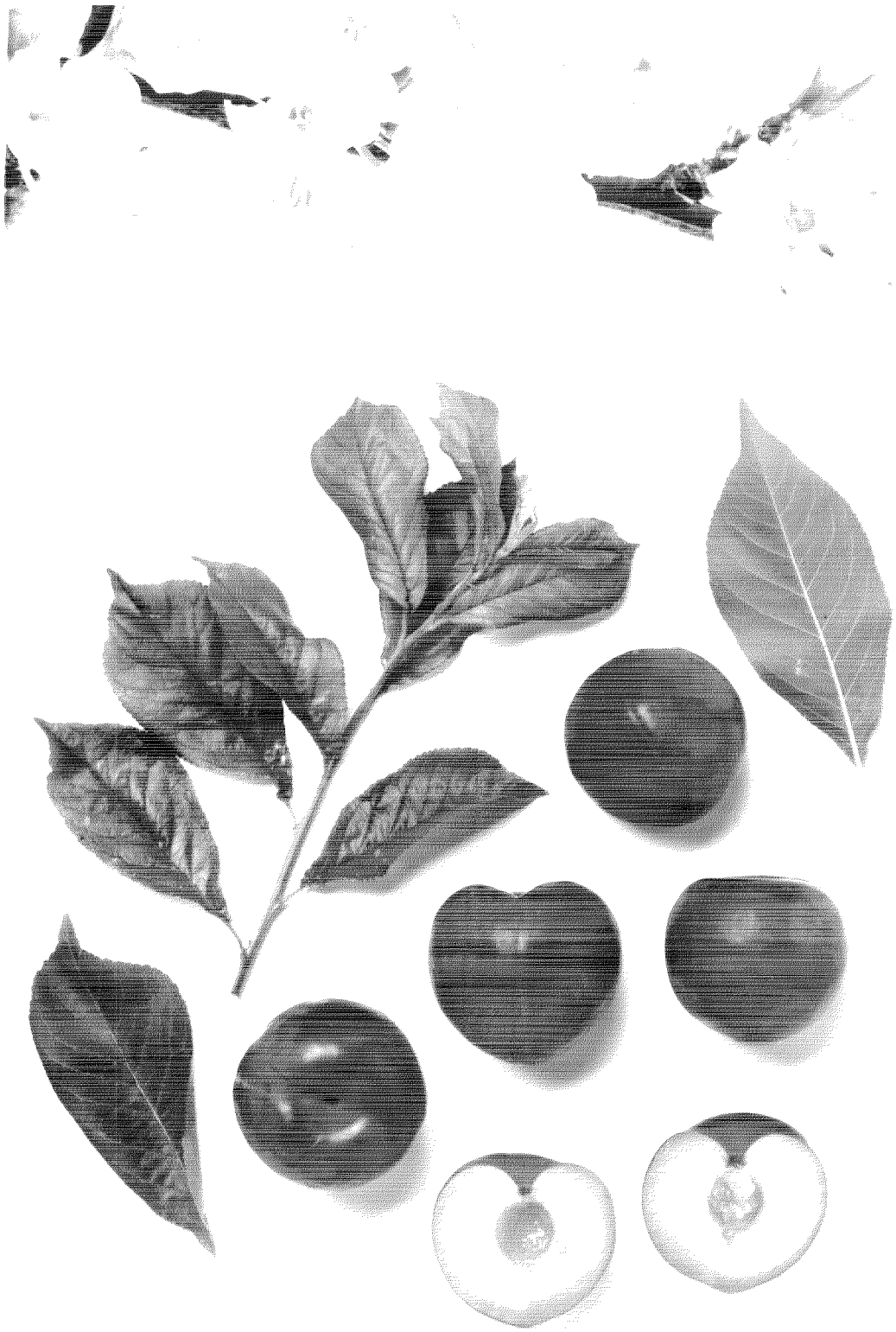

UNITED STATES PATENT AND TRADEMARK OFFICE

CERTIFICATE OF CORRECTION

PATENT NO. : Plant 10,116

DATED : November 11, 1997

INVENTOR(S) : MICHAEL R. GERAWAN

It is certified that error appears in the above-identified patent and that said Letters Patent is hereby corrected as shown below:

Column 1, Line 30, delete "unatractive" and substitute ---unattractive---.

Column 4, Line 35, delete "8J-10)." and substitute ---8-J-10).---.

Column 4, Line 44, delete "inwads" and substitute ---inwards---.

Column 7, Line 14, delete "characeristics" and substitute ---characteristics---.

Signed and Sealed this

Twenty-seventh Day of January, 1998

Bruce Lehman

*Attest:*

BRUCE LEHMAN

*Attesting Officer*

*Commissioner of Patents and Trademarks*